United States Patent
Kovesdi et al.

(12) 
(10) Patent No.: US 6,511,823 B1
(45) Date of Patent: Jan. 28, 2003

(54) HEPARIN BINDING NEUROTROPHIC FACTOR GENE SEQUENCE

(75) Inventors: Imre Kovesdi, Pearl River, NY (US); Peter Bohlen, Peekskill, NY (US)

(73) Assignee: American Cyanamid Corporation, Stamford, CT (US)

( * ) Notice: Subject to any disclaimer, the term of this patent is extended or adjusted under 35 U.S.C. 154(b) by 0 days.

(21) Appl. No.: 07/568,574

(22) Filed: Aug. 20, 1990

(51) Int. Cl.$^7$ .......................... C07H 21/04; C12Q 1/68; C12N 15/63
(52) U.S. Cl. .................. 435/69.1; 435/320.1; 435/325; 536/23.1
(58) Field of Search .............................. 435/69.1, 69.4, 435/320.1, 325; 935/66; 536/24, 23.1

(56) References Cited

U.S. PATENT DOCUMENTS 5,171,842 A * 12/1992 Bohlen et al. ............... 530/350

FOREIGN PATENT DOCUMENTS

EP 0326075 * 8/1989

OTHER PUBLICATIONS

Stryer 1988 Biochemistry, 3$^{rd}$ Ed., Freeman & Co., N.Y. pp. 120–123.*
Maniatis et al. 1982. Molecular Cloning: a Laboratory Manual, Cold Spring Harbor Lab., SCH, N.Y. pp. 226–227, 412, 413, 422, 511, 515, & 518.*
Bohler et al. J Cell. Biochem. Supp. 12A. 1988: D401.*
Rauvala EMBO J vol. 8: 2933. 1989.*
Milner et al. Biochem. Biophy Res Com. 165:1096 1989.*
Suggs et al. PNAS 78:6613.1981.*

* cited by examiner

*Primary Examiner*—Andrew Wang
(74) *Attorney, Agent, or Firm*—Elizabeth Barnhard; Joseph M. Sorrentino (57) ABSTRACT

The invention relates to Novel DNA and amino acid sequences for a heparin bending neurotrophic factor, (HBNF). Also described are expression vectors and host cells useful in a method for production of the HBNF protein.

12 Claims, 7 Drawing Sheets

```
   1 AAGTAAATAAACTTTAAAAATGGCCTGAGTTAAGTGTATTAAAAAGAAGAAATAGTCGTAAGATGGCAGT
  71 ATAAATTCATCTCTGCTTTTAATAAGCTTCCCAATCAGCTCTCGAGTGCAAAGCGCTCTCCCTCCCTCGC
 141 CCAGCCTTCGTCCTCCTTCCTGGCCCGCTCCTCCATCCTCCCCATTCTCCCTTCCCTTCGTCCCTCCCTG
 211 TCAGGGCGTAATTGAGTCAAAGGCAGGATCAGGTTCCCCGCCTTCCAGTCCAAAAATCCCGCCAAGAGAG
 281 CCCCAGAGCAGAGAGCAGCAGCGCGCCCAAGCAGGAGAGGGAAGAGAGACCAGTGAGTCATCCGTCAGAAG
 351 GCGGGGAGGAGCAGCAGCCAAGCAGGCAGCTGCAGCAGAGCTGCAGCGGGTACCTGGACTCAGCGGTAGCAACC
 421 TCGCCCCTTGCAACAAAGGCAGACTGAGCGCCAGAGAGGACGTTTCCAACTCAAAA

477 ATG CAG GCT CAA CAG TAC CAG CAG CAG CGT CGA AAA TTT GCA GCT GCC TTC TTG
 -32  M   Q   A   Q   Q   Y   Q   Q   Q   R   R   K   F   A   A   A   F   L

531 GCA TTC ATT TTC ATA CTG GCA GCT GTG GAT ACT GCT GAA GCA GGG AAG AAA GAG
 -14  A   F   I   F   I   L   A   A   V   D   T   A   E   A   G   K   K   E

585 AAA CCA GAA AAA AAA GTG AAG AAG TCT GAC TGT GGA GAA TGG CAG ACT CGG ACT
   5  K   P   E   K   K   V   K   K   S   D   C   G   E   W   Q   T   R   T

639 TGT GTG CCC ACC AGT GGA GAC CAA TGT GGG CTG GGC GAG GGC ACA CGG TGC AAC
  23  C   V   P   T   S   G   D   Q   C   G   L   G   E   G   T   R   C   N

693 GGA GCT GAG TGC AAG CAA ACA CCA AAG ATG ACC CAG AGA TGT GAA AAG ATC CCC AAC
  41  G   A   E   C   K   Q   T   Q   K   M   T   Q   R   C   K   I   P   N

747 TGG AAG CAA TTT GGC GAG GCG CTG AAG TGC CAG AGT CTG AAG CCC TGT TGG GGA GAA
  59  W   K   Q   F   G   A   E   C   Q   S   L   K   P   C   A   W   G   E

801 TGT GAC CTG AAC ACA GCC CAG AAG ACT GTC ACC ATC TCC AAG AAA AAG GCC CTG
  77  C   D   L   N   T   A   Q   K   T   V   T   I   S   K   K   R   A   L

855 CAC AAT GCC GAA CCC AAA CCT GAA TCT AAG AAG AAA AAG GAA GGC AAG AAA
  95  H   N   A   E   P   K   P   E   S   K   K   K   K   E   G   K   K

909 ACC AAG CCC AAA CCT CAA GAA CAA GCA TAA
 113  T   K   P   K   P   Q   E   Q   A   *

963 CAG GAG AAG ATG CTG GAT TAA
 131  Q   E   K   M   L   D   *

984 AAGATGTCACCTGTGGAACATAAAAAGGACATCAGCAAACAGGATCAGTTAACTATTGCATTTATATGTA
1054 CCGTAGGCTTTGTATTCAAAAATTATCTATAGCTAAGTACACAATAAGCAAAAACAACCAATTTGGGTTC
1124 TGCAGTACATAGAAGTTGCCATCTTCTTGCCATCCGCCATTCGAATTTCAGTTCTGTACATCTGC
1194 CTATATTCCTTGTGATAGTGCTTTGCTTTTTCATAGATAAGCTTCCTGTCCTTTCGAAGCATCTTTT
1264 GGGCAAACTTCTTTCTCAGGCGCTTCAGCTCTGCGAAATTCCTTCGCTTTTTTCTTAAGGGTTTC
1334 TGGCACAGCAGGAACCTCCTTCCTTCCTTCTACACCCCTCTATGTACC
```

HEART

LUNG

BRAIN

THYMUS

STOMACH

LEG MUSCLE

LIVER

KIDNEY

SPLEEN

Figure 3B

HUMAN

MOUSE

Gly-Lys-Lys-Glu-Lys-Pro-Glu-Lys-Lys-Val-Lys-Lys-Ser-Asp-Cys-Gly-Glu-Trp-Gln-Trp-
5              10              15              20

Ser-Val-Cys-Val-Pro-Thr-Ser-Gly-Asp-Cys-Gly-Leu-Gly-Thr-Arg-Glu-Gly-Thr-Arg-Thr-
25             30             35             40

Gly-Ala-Glu-Cys-Lys-Gln-Thr-Met-Lys-Thr-Gln-Arg-Cys-Lys-Ile-Pro-Cys-Asn-Trp-Lys-
45            50            55             60

Lys-Gln-Phe-Gly-Ala-Glu-Cys-Lys-Tyr-Gln-Phe-Gln-Ala-Trp-Gly-Glu-Cys-Asp-Leu-Asn-
65            70            75             80

Thr-Ala-Leu-Lys-Thr-Arg-Thr-Gly-Ser-Leu-Lys-Arg-Ala-Leu-His-Asn-Ala-Asp-Cys-Gln-
85            90            95           110

Lys-Thr-Val-Thr-Ile-Ser-Lys-Pro-Cys-Gly-Lys-Leu-Thr-Lys-
105           110

HEPARIN BINDING NEUROTROPHIC FACTOR GENE SEQUENCE

This invention relates to a novel DNA sequence for a heparin-binding neurotrophic factor (HBNF). The sequence of the invention encodes a protein which is capable of inducing nerve cell growth and differentiation, as well as nerve cell maintenance and repair, both in vivo and in vitro.

The protein in question is normally produced in the human brain and homologous forms exist in a number of different species. The proteins have also been previously referred to as a heparin-binding brain mitogens (HBBMs). Although the purified proteins are known, the only available source of the proteins has been from brain tissue extracts. The procedure for isolation from brain tissue is laborious and yields relatively small quantities of HBNF.

The gene encoding the human HBNF has now been isolated from a cDNA library obtained from newborn human brain stem RNA. It is a 411 nucleotide sequence predicting a protein having 136 amino acids with a molecular weight of about 15 KD. The gene has been sequenced and expressed in E. coli, and the protein so produced retains the neurotrophic activity of the native HBNF.

BACKGROUND OF THE INVENTION

In recent years a number of relatively small polypeptides, known as growth factors, have been identified and isolated. The term "growth factors" refers to a class of signalling substances which affect the growth and differentiation of certain types of animals; this effect can be seen both in the animal and in tissue culture. A given growth factor may have an effect on more than one type of cell.

Many of the better known growth factors have significant neurotrophic activity, i.e., they are capable of maintaining or stimulating growth of nerve cells. The earliest discovery of such a neurotrophic factor was nerve growth factor (NGF; Gospodarowicz, J. Biol. Chem. 250: 2515–2520, 19757. Similar growth factors which are in the same family as NGF are brain-derived neurotrophic factor (BDNF; Leibrock et al., Nature 341: 149–153, 1989) and neurotrophic factor —3 (NT-3; Maisonpierre et al., Science 247: 1446–1451, 1990). Additional growth factors include ciliary neurotrophic factor (CNTF; Lin et al, Science 246: 1023–1025, 1980, IGF-II (Mill et al, PNAS USA 82: 7126–7130, 1985), activin (Schubert et al., Nature 344: 868–870, 1990) and purpurin (Berman et al., Cell 51: 135–142, 1987).

A number of other known factors fall into a superfamily related to fibroblast growth factor (FGF); this includes basic FGF(bFGF), Esch et al., PNAS USA 81: 5364–5368; PNAS USA 82:6507–6511), acidic FGF (aFGF), (Bohlen et al., EMBO. J. 4 1951–1956, 1985; Gimenez-Gallego et al., Science 230: 1385–1288, 1985), as well as products of the oncogenes int—2 (Dickens and Peters, Nature 326:833, 1984), hst/KS (Delli Bovi et al., Cell 50: 729–737, 1987) FGF-5 (Zhan et al., Mol. Cell Biol. 8:3487–3495, 1988), FGF-6 (Marics et al., Oncogene 4: 335–340, 1989) and KGF (Finch et al., Science 245: 752–755, 1989). These are all (except KGF) mitogens for vascular endothelial cells, and all also bind strongly to heparin. Other heparin-binding growth factors, such as VEGF/VPF, are also known (Keck et al, Science 246: 1309–1312, 1989). These heparin-binding growth factors are also frequently isolated from brain tissue and may play a significant role in the growth and development of brain cells.

A previously unknown heparin binding protein was described in EP 326 075, and was referred to therein as HBBM; it was disclosed as a brain mitogen as well as a tissue formation, maintenance and repair factor, particularly for neural tissue. It is also structurally unrelated to any of the aforementioned growth factors, although it appears to be structurally related to a protein the gene of which was previously referred to as MK (Kadomatsu et al., Biochem Biophys. Res. Comm. 151: 1312–1318, 1288) and a human form of the MK protein. The homology between HBNF and MK genes and proteins is very high, and they are assumed to constitute a new family of neurotrophic factors. The "HBBM" protein is the "HBNF" protein of the present invention. However, as indicated in the aforementioned European Application, it has previously been necessary to isolate the protein directly from brain tissue by a procedure involving several chromatographic steps, as neither the complete protein sequence nor the gene sequence was previously known.

More recently, HBNF proteins have been isolated from both rat (Rauvala, EMBO J. 8: 2933–2941, 1989; Huber et al Neurochem Res. 15: 435–439, 1990), and cow (Milner et al., Biochem. Biophys. Res. Comm. 165: 1096–1103, 1989; Huber et al Neurochem Res. 15:435–439, 1990), and the amino terminal sequences have been determined. Similarly, the N-terminal amino acid sequences of the human and chicken proteins have been determined (EP 326 075; Huber et al, Neurochem. Res. 15: 435–439, 1990). Moreover, no determination of the DNA sequence of the HBNF has previously been achieved. The present invention now provides an entire gene sequence for human HBNF, as well as cloning vectors and host cells capable of expressing the gene and producing pure HRNF protein. The invention also provides both in vitro and in vivo methods of promoting nerve cell growth, repair and maintenance.

BRIEF DESCRIPTION OF THE DRAWINGS

FIG. 1 relates to complementary DNA cloning, nucleotide and deduced amino acid sequence of human HBNF. (a) Diagram of four overlapping partial cDNAs encoding HBNF. Top line indicates the MRNA with black and hatched boxes representing the HBNF coding region and postulated 3'poly(A) tract respectively. Restriction sites: H=HindIII, K=Kpnl, P=PstI; nt=nucleotide length of clones. (b) Combined nucleotide sequence of clones HHC7, 8, 10 and 12 with deduced amino acid sequence (single-letter code). Amino acids shown in normal type indicate the 136 amino acids of mature human HBNF preceded by an additional 32 boldfaced amino acids representing a potential 168 amino acid precursor protein. Underlined amino acid sequences indicate the two peptides utilized for the design of oligonucleotide probes used in cloning the gene. The three nucleotides missing in clone HHC7 are boxed and the start of the mature protein indicated by an arrow.

FIG. 2 illustrates expression and functional characterization of human HBNF protein. (a) SDS-PAGE gel electrophoresis of HBNF protein samples. Protein standards were from BRL. Lane N, purified bovine HBNF protein (100 ng), Lanes + and − isopropyl-B-D-thio-galactopyranoside (IPTG) induced and uninduced cultures containing the bacterial expression construct pETHH8. (b) Neurite outgrowth assay in rat brain neurons in the absence (A) or in the presence of rat brain HBNF (320 ng/ml) (B), purified bacterially produced human HBNF (160 ng/ml) (C) or (320 ng/ml) (D).

FIG. 3 shows Northern blot analysis of HBNF mRNA in tissues of the adult mouse and human. (a) From each tissue, heart, lung, brain, thymus, stomach, leg muscle, liver, kidney, spleen; 20 ug total RNA was applied per lane. (b) RNA analysis comparing 10 ug total RNA from adult mouse and human brain.

FIG. 4 shows expression of the HBNF gene during rat embryogenesis. From each tissue 20 ug of total RNA was applied per lane and hybridized with a $^{32}$p-labeled human HBNF cDNA probe. Tissues used in the RNA isolation were total embryo proper for E8 and E10, heads for E12 and E14, total brain for E16, E18, E20, P2 and Adult.

SUMMARY OF THE INVENTION

The present invention relates to a novel purified gene and DNA sequence which encodes a heparin binding neurotrophic factor, referred to here as HBNF. Also disclosed is a complete amino acid sequence for the human protein, and a partial amino acid sequence for the bovine protein.

The availability of the gene sequence permits the expression of the HBNF protein in a variety of host cells. Thus, the invention also relates to a method for production of a purified HBNF protein which comprises transforming a host cell with an HBNF gene and culturing the host cell under conditions which permit expression of the gene in the host cell. Recovery of the HBNF protein may be made either from the culture supernatant or directly from the host cell, depending on the method of expression in the host. Transformation of host cells may be achieved either directly by naked DNA or by expression vectors engineered to carry the DNA sequence encoding human HBNF. The invention therefore also encompasses host cells transformed with the claimed DNA sequence, as well as expression vectors comprising the sequence.

The HBNF protein is useful in maintenance, growth and repair of tissue, particularly neural tissue. Thus the invention also relates to therapeutic methods which comprise administering effective amounts of the HBNF in vivo to an individual in need of such treatment. This may be achieved by direct administration of the purified protein, or may also be achieved by transplant of transgenic host cells capable of producing the protein, into the region of the body needing such treatment.

The purified HBNF protein also has utility as a component in cell culture, particularly in neural cell culture, to maintain the cells growing therein.

DETAILED DESCRIPTION OF THE INVENTION

Figure 1A:
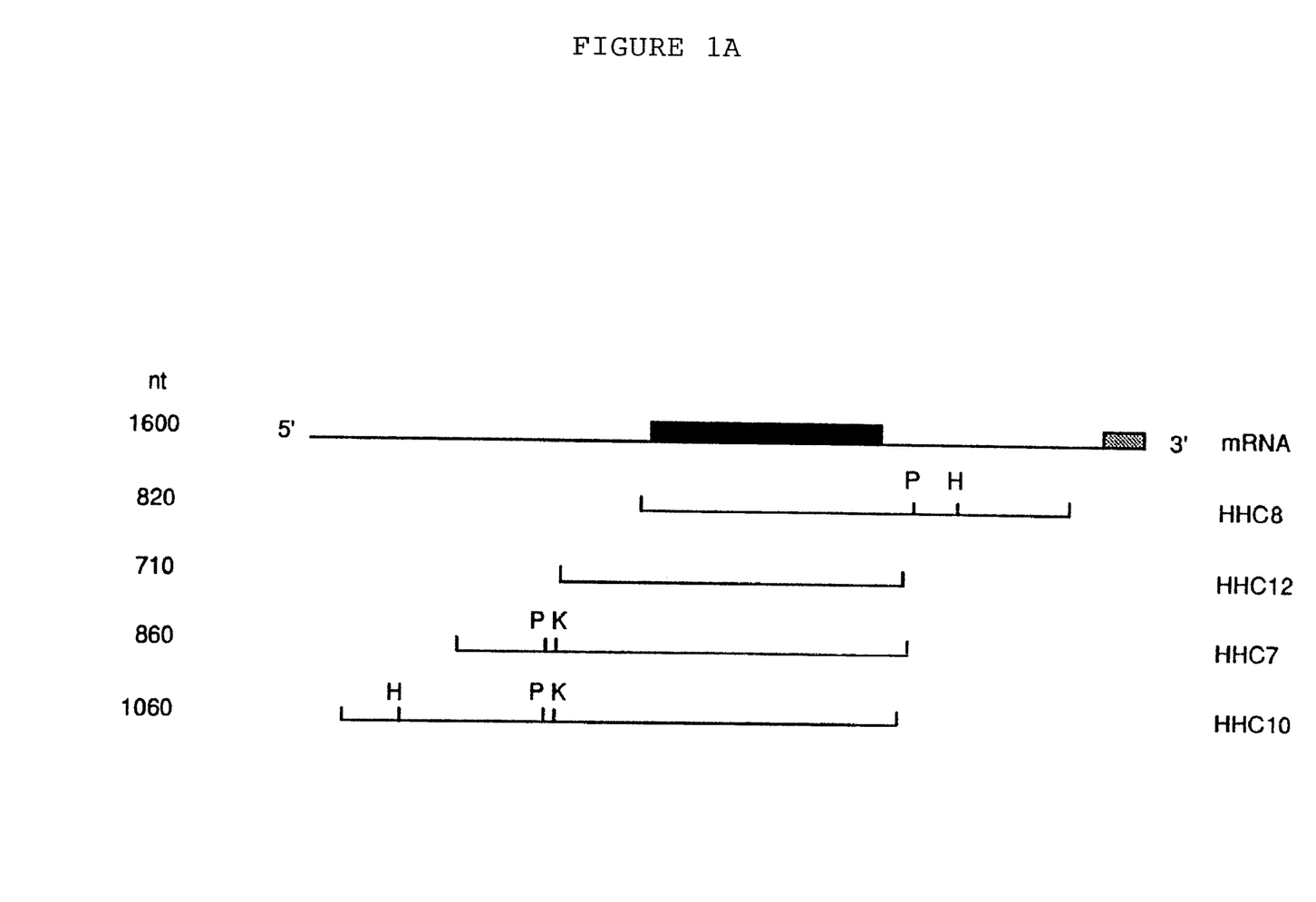

The human DNA sequence encoding HBNF is cloned by utilizing a combination of polymerase chain reaction (PCR) and screening of a cDNA library derived from newborn human brainstem cells. Bovine HBNF amino acid sequence is used as a starting point for designing oligoucleotides for a PCR amplification reaction. A partial 114 amino acid sequence of bovine HBNF is provided in FIG. 5. It is expected that the total length of the protein is 136 amino acids, as is the human protein. Poly (A)+ RNA from adult rat brain is reverse transcribed to produce a complementary cDNA strand. This strand is then used as a template for the PCR reaction, with sequence specific primers. The expected 282 base pair PCR product is then isolated and cloned into an appropriate vector. DNA sequencing identifies the cloned fragment that encodes the rat HBNF peptide. The cloned insert is isolated, labeled, and used as a probe to screen a phage cDNA library. Of approximately a million and a half phage screened, four candidate cDNA clones all isolated, subcloned and sequenced. The DNA sequence of human HBNF is presented in FIG. 1.

The cDNA sequence indicates that the human HBNF protein is 136 amino acids long. There is a single amino acid difference from the bovine sequence, at residue 98 (Asp in bovine, Glu in human). On the basis of N-terminal protein and cDNA complete sequence information, the expected molecular weight of the protein would be 15 kD, which is smaller than the 18 kD protein previously observed with SDS-PAGE (Rauvala, EMBO J. 8:2933–2941, 1989; Milner et al. Biochem. Biophys. Res. Comm. 154:1096–1103, 1989). Therefore, it is assumed that the observed size difference is due to the effect of the basicity of the protein on its migration on the gel.

Also, two smaller forms of the human protein had been previously identified (EP 326 075); these probably represent C-terminal truncated forms of the full length protein generated by change during extraction/isolation when enzyme inhibitors are absent. A putative methionine translation initiation codon is located 32 amino acids preceding the N-terminal glycine of the mature protein; this presequence is not similar to previously identified signal sequences. (Von Heijne, J. Mol. Bio. 184:99–105, 1985). However, if translation of the protein is initiated at this methionine, the presequence would represent the only hydrophobic region in an otherwise highly hydrophilic protein. The protein processing site preceding the mature HBNF protein, agrees with structural determinants for cleavage of a signal sequence from a mature protein (von Heijne, Nucl. Acids Res. 14: 4683–4690, 1986).

Figure 1B:
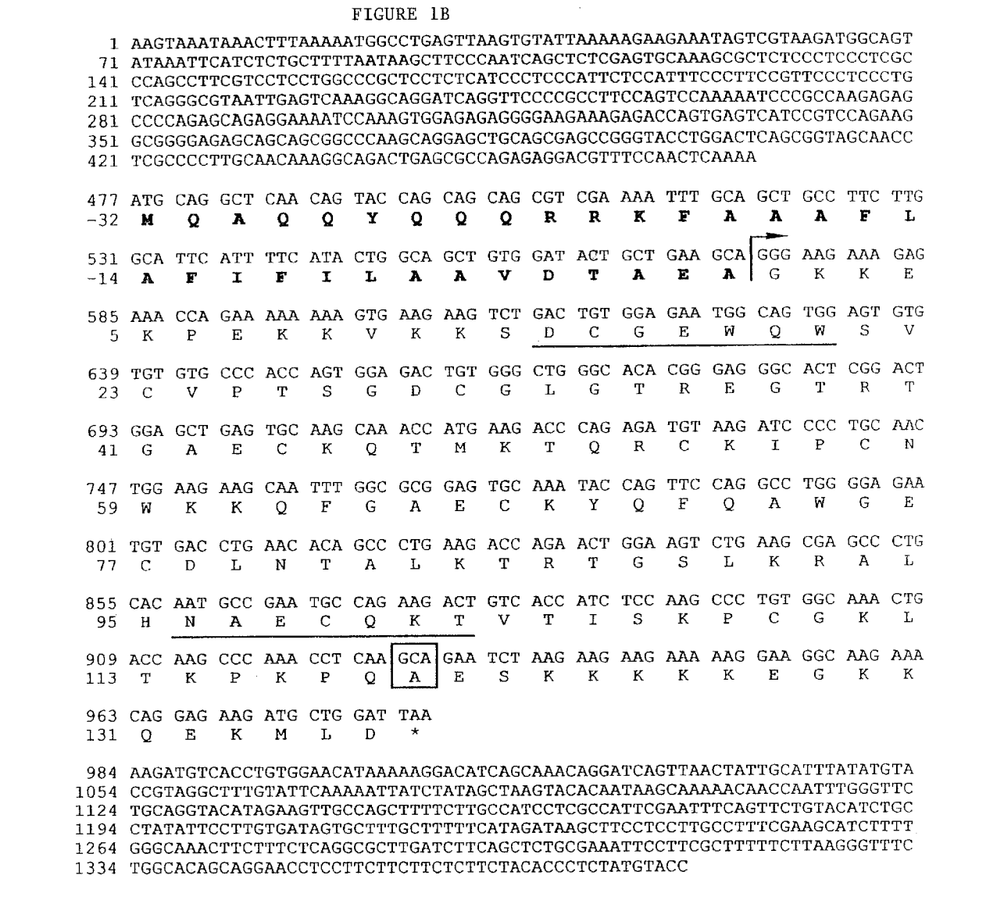
Figure 2A:
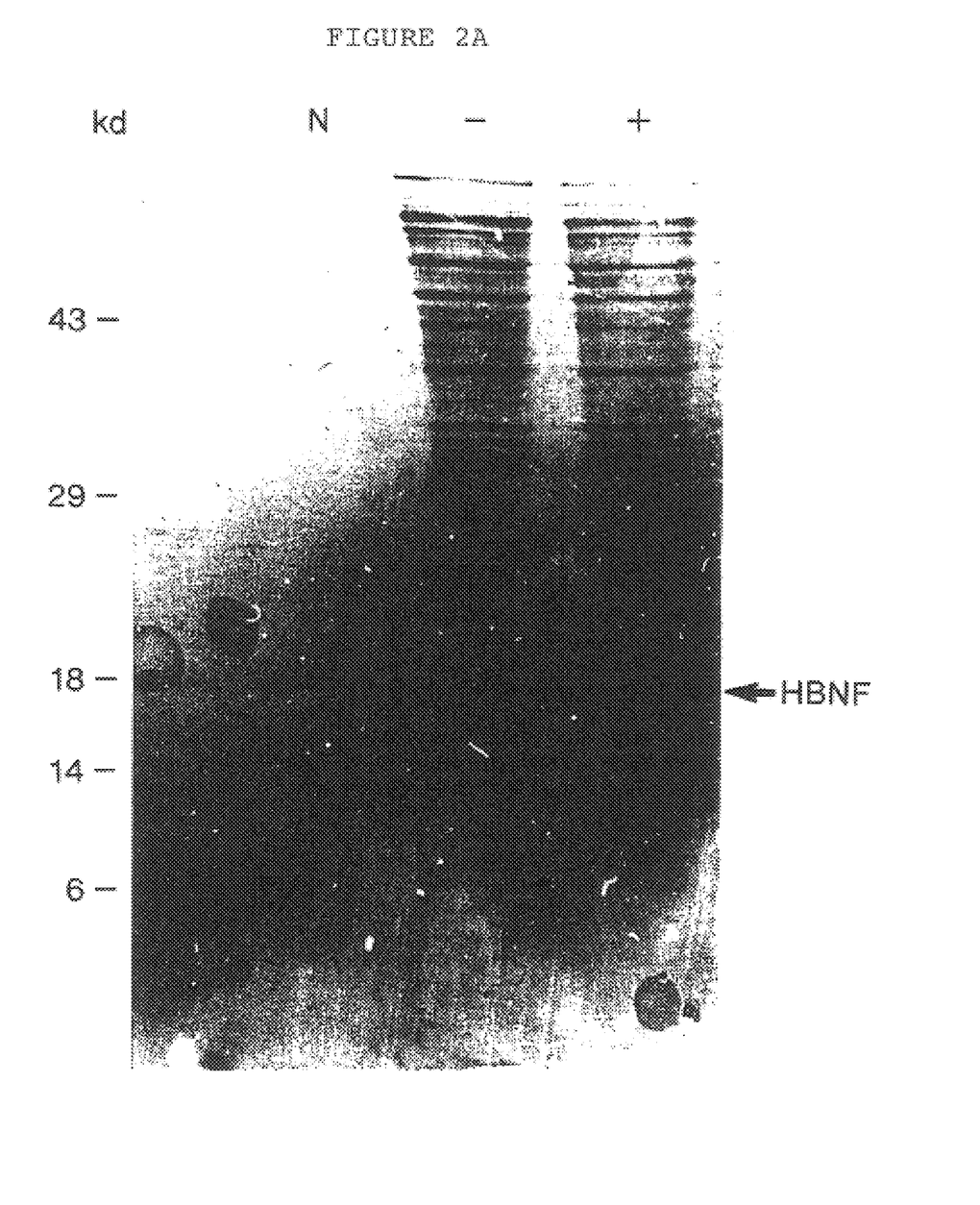

To provide a source of mature human HBNF protein free of contaminating eukaryotic proteins one of the clones, HHC8 is used as template for PCR amplification with primers designed to place a methionine codon immediately 5' to the N-terminal glycine (FIG. 1b). The amplified product is cloned into a modified form of the expression vector pET-3a (Studier et al., Meth. Enzymol. 185: 60–69, 1990) and the resulting plasmid, pETHH8 transformed into strain BL21 LysS (id.). A protein extract of the IPTG-induced culture containing pETHH8 (FIG. 2a lane 3) shows a strong protein band approximately the same size as mature bovine HBNF (lane 1), compared to a faint protein band at the corresponding position for the uninduced culture (lane 2). The fact that bacterially produced HBNF migrates in the same position on SDS-PAGE as bovine and rat-derived HBNF and is biologically active, suggests that there is minimal, if any, posttranslational modification(s) of the native HBNF protein as compared to HBNF expressed in E. coli. The lack of a recognizable glycosylation signal in the HBNF sequence further supports this hypothesis.

Figure 2B:
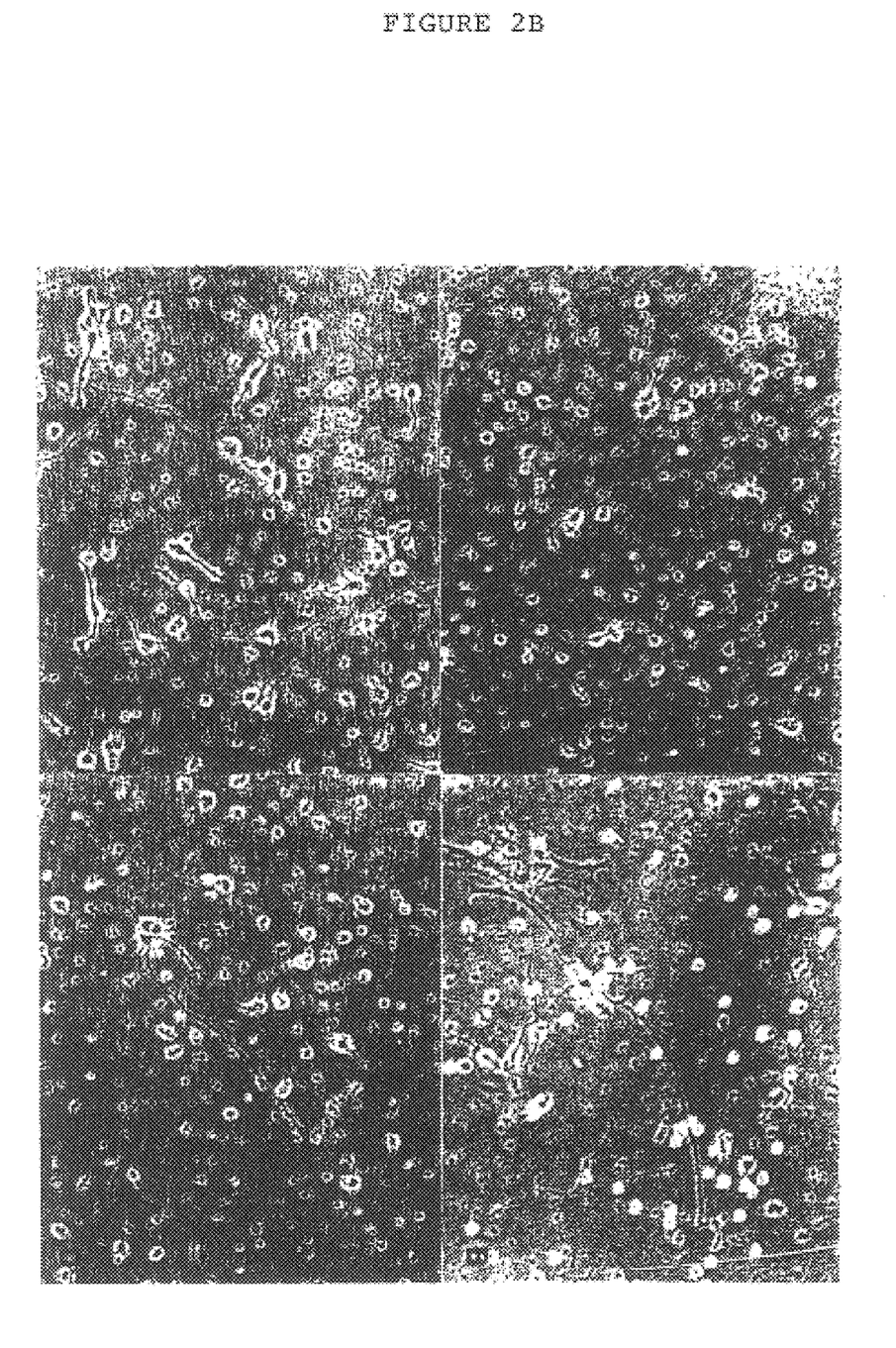

Human HBNF protein is purified from IPTG-induced bacterial cultures by utilizing its affinity for heparin. Its N-terminal amino acid sequence is confirmed by protein sequencing and the protein is assayed for neurotrophic activity in a neurite outgrowth assay. This bacterially derived human HBNF showed activity comparable to that of bovine and rat HBNF (FIG. 2b). Thus, consistent with observations described above, we have found that mature HBNF has neurotrophic activity.

The following examples illustrate the cloning and expression of the HBNF gene in a T7 RNA polymerase expression system. However, although this T7 expression system has proven quite efficient, it is to be understood that this is not the only means by which human HBNF can be produced recombinantly. Production of HBNF can be achieved by incorporation of the HBNF gene into any suitable expression vector and subsequent transformation of an appropriate host cell with the vector; alternately the transformation of the host cells can be achieved directly by naked DNA without the use of a vector. Production of HBNF by either eukaryotic cells or prokaryotic cells is contemplated by the present invention. Examples of suitable eukaryotic cells include mammalian cells, plant cells, yeast cells and insect cells. Similarly, suitable prokaryotic hosts in addition to *E. coli*, include *Bacillus subtilis*.

Other suitable expression vectors may also be employed and are selected based upon the choice of host cell. For example, numerous vectors suitable for use in transforming bacterial calls are well known. For example, plasmids and bacteriophages, such as λ phage, are the most commonly used vectors for bacterial hosts, and for *E. coli* in particular. In both mammalian and insect cells, virus vectors are frequently used to obtain expression of exogenous DNA. In particular, mammalian cells are commonly transformed with SV40 or polyoma virus; and insect cells in culture may be transformed with baculovirus expression vectors. Yeast vector systems include yeast centromere plasmids, yeast episomal plasmids and yeast integrating plasmids.

It will also be understood that the practice of the invention is not limited to the use of the exact sequence of the human HBNF gene as defined in FIG. 1. Modifications to the sequence, such as deletions, insertions, or substitutions in the sequence which produce silent changes in the resulting protein molecule are also contemplated. For example, alteration in the gene sequence which reflect the degeneracy of the genetic code, or which result in the production of a chemically equivalent amino acid at a given site, are contemplated; thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Additionally, since it is primarily the central portion of the protein which is conserved among species, nucleotide changes which result in alteration of the N-terminal and C-terminal portions of the protein molecule, would not be expected to alter the activity of the protein. Indeed, the "HBBM" size variants disclosed in EP 326,075 include C-terminal truncation of the HBNF protein. It may also be desirable to eliminate one or more of the cysteines present in the sequence, as the presence of cysteines may result in the undesirable formation of multimers when the protein is produced recombinantly, thereby complicating the purification and crystallization processes. Each of the proposed modifications is well within the routine skill in the art, as is determination of retention of biological activity of the encoded products. Therefore, where the phrase "HBNF DNA sequence" or "HBNF gene" is used in either the specification and the claims, it will be understood to encompass all such modifications and variations which result in the production of a biologically equivalent HBNF protein. In particular, the invention contemplates those DNA sequences which are sufficiently duplicative of the sequence of FIG. 1 so as to permit hybridization therewith under standard high stringency southern hybridization conditions, such as those described in Maniatis et al., (Molecular Cloning. A Laboratory Manual. Cold Spring Harbor Laboratory, 1982)

As noted above, and as shown in the examples below, the protein encoded by the HBNF gene sequence has been shown to have neurotrophic activity in vitro. Specifically, the protein, when added to perinatal neurons in culture, stimulates neurite outgrowth. As such, the HBNF proteins are useful both in vivo and in vitro, in growth, maintenance and repair of nerve cells of the peripheral and central nervous systems. An example of in vitro application is in maintenance of embryonic brain implants which are now proposed for use in treatment of Parkinson's disease.

In vivo administration of HBNF is significantly simplified by the discovery of the gene sequence, particularly in treatment of central or peripheral nervous system injury. The identification of the gene and its sequence permit construction of transgenic cells such as fibroblasts, monocytes, or macrophages, which may be engineered to permit expression of the HBNF gene and used as an implant for treatment of neurodegenerative disorders, peripheral nerve repair following surgery, or any conditions in which enhancement of nerve cell growth and/or repair would be desirable.

Moreover, the therapeutic use of HBNF is not limited to treatment of humans alone. In fact, in view of the conserved nature of this protein among distantly related species, administration of HBNF in any form may be beneficial for veterinary application as well. Therapeutic compositions comprise HBNF in amounts sufficient to produce the desired biological effect, in combination with a pharmaceutically acceptable liquid or solid carrier. Alternately, the composition comprises a pharmaceutically acceptable aggregation of compatible transgenic cells capable of expressing HBNF in vivo, as an implant for peripheral and central nervous system repairs or differentiation treatment.

In view of the apparent role of HBNF in differentiation the protein is also proposed as a general tissue differentition factor. In particular, HBNF may be useful in treatment of tumor cells to induce reversion to differentiated state.

The following example is presented for purposes of illustration only, and is not to be considered as limiting the scope of the present invention.

EXAMPLE

(1) HBNF Protein Purification and Amino Acid Sequence Analysis

Figure 5:
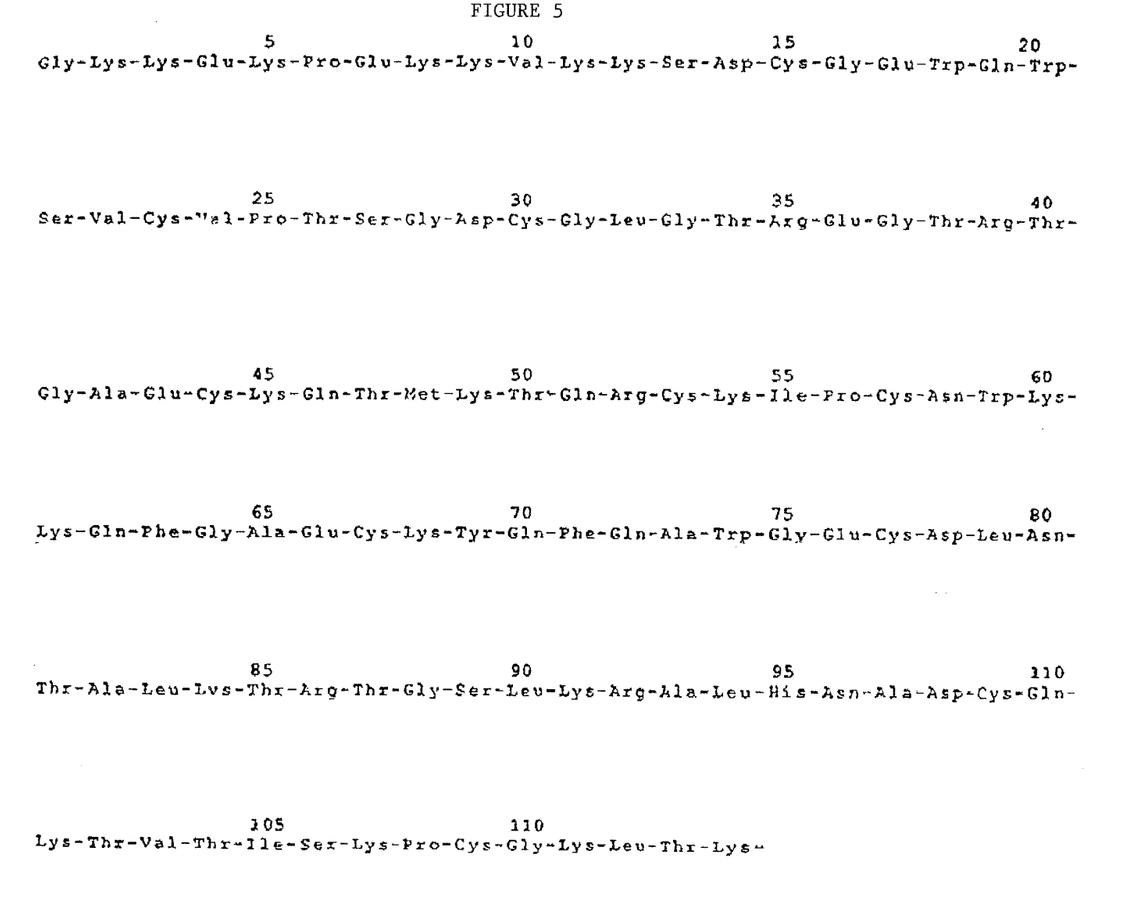
FIG. 5 shows a partial, 114 amino acid sequence of bovine HBNF.

HBNF protein is isolated from bovine brain by protocols described previously in EP 326 075, which is incorporated herein by reference in its entirety. Briefly, reverse-phase HPLC-purified HBNF is chemically modified by reduction in mercaptoethanol and alkylation of cysteine residues with iodo-(2-14C)-acetic acid according to a procedure described previously (Gautschi-Sova et al, Biochem. Biophys. Res. Comm 140: 1874–1880, 1986) Carboxymethylated protein is purified by reverse-phase HPLC using a Brownlee Aquapore C8 column (25×0.46 cm 7 um particle size, Applied Biosystems) using as the mobile phase 0.1% trifluoroacetic acid in an acetonitrile gradient. Aliquots corresponding to 3 nmol of carboxymethylated HBNF are diluted with enzyme digestion buffer to reduce the acetonitrile concentration of the sample to approximately 10% and digested with the following proteases: *Staphylococcus aureus* V8 (cleavage after glutamic acid residues), Arg-C (cleavage after arginine), Asp-N (cleavage before aspartic acid) and chymotrypsin (preferential cleavage after aromatic residues). Enzymes are from Boehringer Mannheim and cleavage is performed essentially as suggested by the manufacturer. After digestion, peptides are separated by reverse-phase HPLC on a C8 column using a 90-min linear gradient of acetonitrile in 0.1% trifluoroacetic acid for peptide elution (acetonitrile content at start: 12–16%, at end: 30–44%, depending on the type of digest). In order to ascertain homogeneity of purified peptides, fractions containing peptide material are subjected to a second reverse-phase HPLC step (C8 column, 0.1% heptafluorobutyric acid in an appropriate shallow acetonitrile gradient). Aliquots of 5–500 pmol of isolated peptides are sequenced on an Applied Biosystems 477A gas/liquid-phase microsequenator. Phenyl thiohydantoin (PTH) amino acid derivatives are identified on a Model 120A on-line PTH amino acid analyzer (Applied Biosystems). Experimental protocols for both procedures are as supplied by the instrument manufacturer. The sequence of the first 114 amino acids (out of an expected 136) is shown in FIG. 5.

(2) Polymerase Chain Reaction (PCR)

The bovine HBNF amino acid sequence is used to design degenerate oligonucleotides from the PCR amplification reaction. A completely degenerate sense primer is made to the amino acid sequence: DCGEWOW (FIG. 1) starting with a HindIII restriction site and comprised of the DNA sequence:
5'-CAAGCTTGGAPyTGPlGGNGAPuTGGCAPuTGG-3'.
A completely degenerate antisense primer is made to the amino acid sequence: NADCOKT (FIG. 1.) starting with an EcoRI restriction site and comprised of the DNA sequence:
5'-GGAATTCCGTPyTTPyTGPuCAPuTCNGCPuTT-3'

Total rat brain RNA is isolated from the brains of Sprague-Dawley rats by the guanidinium isothiocyanate-cesium chloride method and poly (A)+RNA is selected by two cycles of binding to oligo (dT)–cellulose (Aviv and Leder, PNAS USA69: 14088–1412, 1972). The rat brain poly (A)+RNA is reverse transcribed with oligo (dt) and AMV-reverse transcriptase (Maniatis et al., Molecular Cloning. A Laboratory Manual. Cold Spring Harbor Laboratory, Cold Spring Harbor, N.Y. 1982.) The PCR reaction is carried out on the complementary DNA template, with 30 cycles, with one minute annealing at 50° C., two minutes extension at 72° and one minute denaturation at 94° C. for 30 cycles using Tag DNA polymerase (USB).

(3) Cloning and Sequencing of Human HBNF

The 282 base pair rat HBNF PCR product is cloned into Blue Scribe (+) vector (Stratagene) and used as a probe in screening a newborn human brainstem and basal ganglia λ gt 11 cDNA library (Kamholz, PNAS USA 83:4962–4966, 1986). Thirty HHC clones are initially identified and after preliminary restriction analysis, four clones are isolated, subcloned in the EcoRI site of Blue Scribe (+), and sequenced by the dideoxynucleotide chain termination method (Sanger et al, PNAS USA 74: 5463–5467, 1988).

Three of the clones have identical sequences in the coding region and the fourth clone has a three-nucleotide in-frame deletion resulting in the removal of an alanine at position 119. These sequences are illustrated in FIG. 1.

(4) Expression of Recombinant HBNF

Clone HHC8 (FIG. 1a) is chosen for use as a template for PCR amplification with primers designed to place a methionine codon and an NdeI restriction site immediately 5' to the N-terminal glycine. The purified PCR product is cloned into a derivative of the expression vector pET-3a, which is modified by the deletion of the 1400 bp Sa11/PvuII fragment and insertion of an f1 origin of replication into the EcoRI site. After sequencing the insert to confirm the fidelity of the PCR amplification, the plasmid (named pETHH8) is transformed into strain BL21 lysS and induced for protein production with IPTG as described (Studier et al, Supra). Pellets from one ml cultures are resuspended in 100 ul of SDS buffer (Laemmli, Nature 227: 680–685, 1970) and 2.5 ul run on a 15% acrylamide SDS-PAGE gel. The gel is stained with coomassie blue. Native HBNF is purified from rat brains and recombinant HBNF from bacterial extract on heparin sepharose CL-6B (Pharmacia) resin in 10 mM Tris, pH 7.0 and eluted with a gradient from 0–2 M NaCl at 1–1.13 M NaCl. Further purification is achieved on Mono S (Pharmacia) columns in 50 mM sodium phosphate, pH 6.8, using a gradient of increasing salt concentration from 0 to 1 M NaCl for elution.

(5) Assay for HBNF Neurotrophic Activity

To determine the neurotrophic activity of recombinant HBNF, observations are made on its ability to stimulate rat brain neuron in comparison with native rat brain HBNF. The procedure is conducted according to the method of Rauvala and Pihlaskari (J. Biol. Chem. 262: 16625–16635, 1987) using recombinant HBNF eluted from Mono S at 0.6 M NaCl as outlined above. Brains from 18 day fetal rats are removed under sterile conditions. The brains are dispersed to single cells in DMEM containing 10% FCS using a sterile 5 ml syringe. The cell suspension is centrifuged for 1–2 minutes at 500 RPM and the supernatant removed and subjected to cell count in a Coulter counter. The concentration is adjusted to 5×105 cells/ml in DMEM/10% FCS, and the cell suspension placed on tissue culture dishes that have been precoated for 30 minutes at room temperature with 50 ug/ml of poly-c-lysine. Cultures are incubated for 24 hours at 37° C., 10% $Co_2$, after which the media is changed to DMEM containing 1 mg/ml BSA, and HBNF is added at the following concentrations: Rat brain HBNF 320 mg/ml; Recombinant human HBNF—160 ng/ml and 320 ng/ml. The results shown in FIG. 2b indicate that recombinant HBNF has neurotrophic activity equivalent to that of native rat HBNF.

(6) Expression of HBNF in Mouse Tissues

Figure 3A:
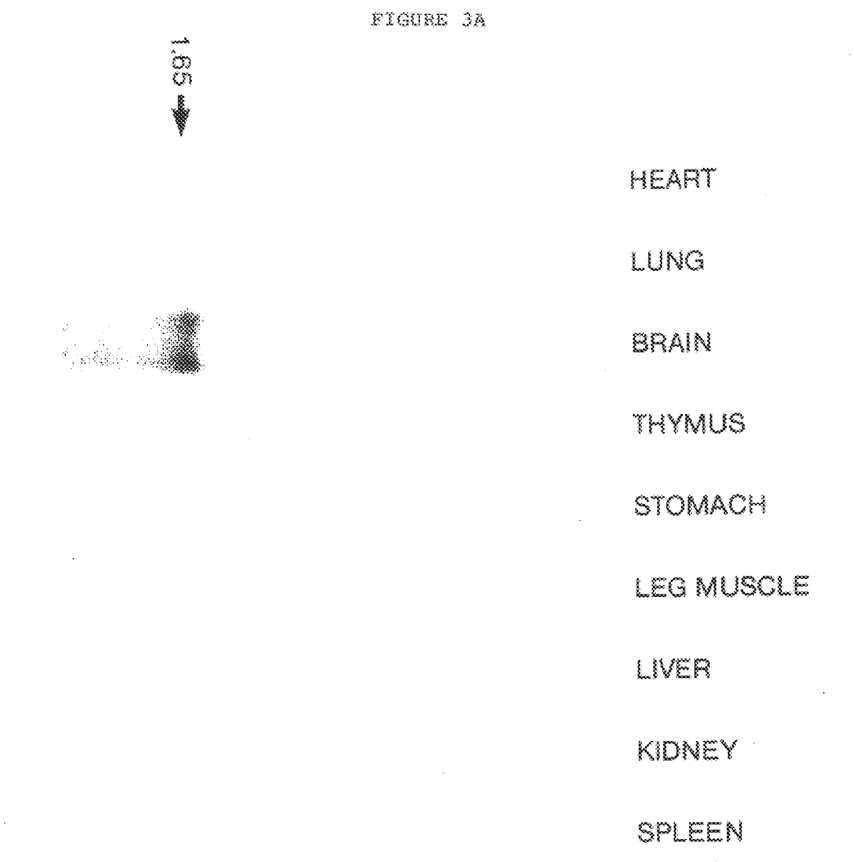
Figure 3B:
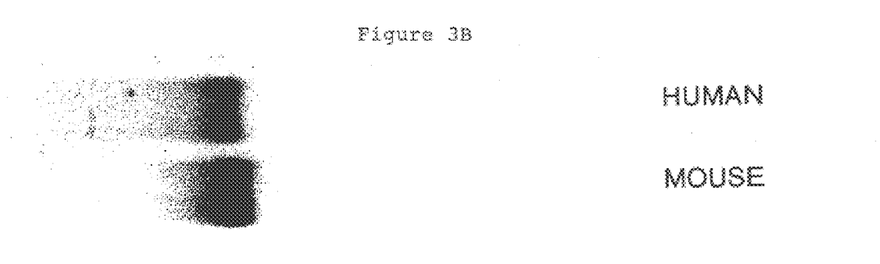
Figure 4:
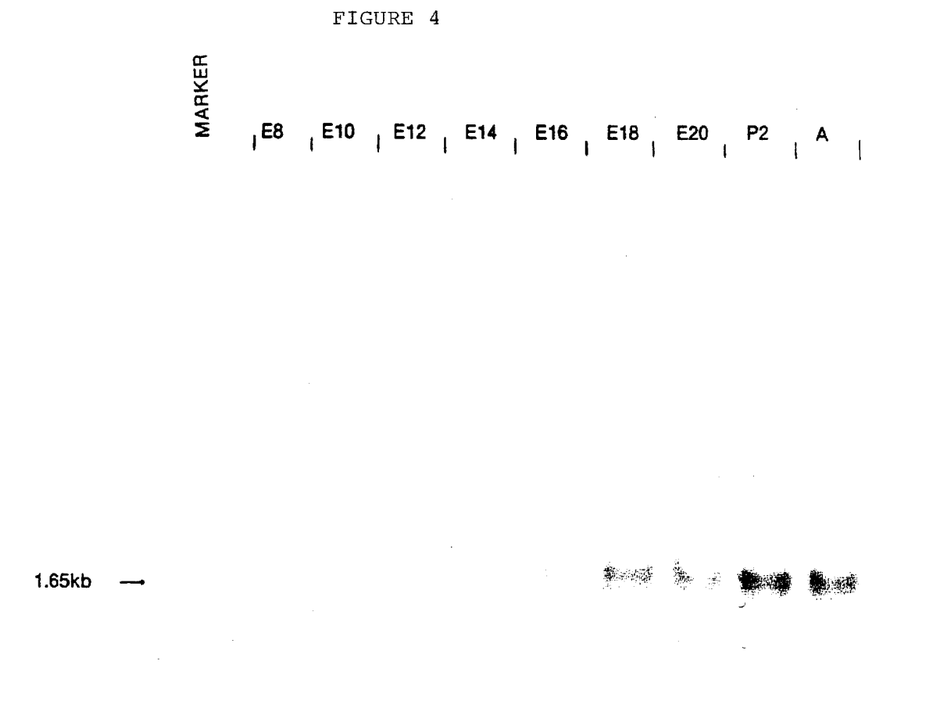

The expression of the HBNF gene is investigated in mouse tissues. Total cellular RNA is isolated by the guanidinium isothiocyanate-cesium chloride method, analyzed on 1% agarose gel containing 0.66 M formaldehyde and blotted onto nylon membrane filter formamide with $^{32}P$ labeled cDNA probes prepared by random oligonucleotide priming. The filters are washed at 65° C. in 1×SSC (0.15 M NaCl, 15 mM Na-citrate pH 7.0), 0.2% SDS and exposed to X-ray films. Northern hybridization analysis of mouse RNA from a variety of tissues using human HBNF cDNA as probe indicates that only the brain expressed a 1650 nucleotide message (FIG. 3a). This is consistent with previous investigations on the localization of HBNF protein, which show it is present only in the brain (Huber et al, supra; Rauvala et al. EMBO J. 8:2933–2941, 1989) in contrast to a recent report also indicating its presence in bovine uterus (Milner et al; Biochem. Biophys. Res. Comm. 165: 1096–1103, 1989). Analysis of total human RNA indicates that the human mRNA is approximately 1600 nucleotides in length, slightly shorter than that of the mouse (FIG. 3b).

(7) Deposit of Biological Materials

An E. coli, strain BL 21 1sS, harboring plasmid pETHH8, has been deposited in American Cyanamid Company's Culture Collection maintained in Pearl River, N.Y., and with the American Type Culture Collection, 12301 Parklawn Drive, Rockville, Md., on Aug. 13, 1990, under accession number ATCC 68385.

What we claim is:

1. A purified and isolated gene encoding heparin binding neurotrophic factor (HBNF) protein comprising the nucleotide sequence set forth in FIG. 1.

2. A method for production of substantially pure HBNF protein which comprises transforming a host cell with the gene of claim 1 and culturing the host cell under conditions which permit expression of the gene by the host cell.

3. The method of claim 2 in which the host cell is *E. coli*.

4. The method of claim 4 in which the gene is in an expression vector pETHH8.

5. An expression vector comprising the gene of claim 1.

6. The vector of claim 5 which is a virus, a plasmid, a yeast vector, or a bacteriophage.

7. The vector of claim 6 which is a plasmid.

8. The vector of claim 7 which is pETHH8.

9. A host cell comprising the gene of claim 1.

10. The cell of claim 9 which is *E. coli*.

11. The cell of claim 10 which comprises a plasmid expression vector.

12. The cell of claim 11 which is deposited with the American Type Culture Collection as ATCC 68385.

* * * * *